United States Patent
Davis et al.

(10) Patent No.: US 8,656,925 B2
(45) Date of Patent: Feb. 25, 2014

(54) BITE BLOCK DEVICE

(75) Inventors: Layne Davis, Juliette, GA (US);
Christopher Menard, Forsyth, GA (US)

(73) Assignee: Surgovations, LLC, Forsyth, GA (US)

( * ) Notice: Subject to any disclaimer, the term of this patent is extended or adjusted under 35 U.S.C. 154(b) by 193 days.

(21) Appl. No.: 13/284,295

(22) Filed: Oct. 28, 2011

(65) Prior Publication Data
US 2013/0104912 A1    May 2, 2013

(51) Int. Cl.
*A61C 5/14*  (2006.01)
*A61C 3/00*  (2006.01)
*A61M 16/00* (2006.01)

(52) U.S. Cl.
USPC .......................... 128/861; 433/6; 128/207.15

(58) Field of Classification Search
USPC ................. 128/861, 859, 857, 846, 207.14, 128/207.15; 433/2, 6
See application file for complete search history.

(56) References Cited

U.S. PATENT DOCUMENTS

| | | | |
|---|---|---|---|
| 2,521,084 A | 9/1950 | Oberto | |
| 2,669,988 A | 2/1954 | Carpenter | |
| 2,882,893 A | 4/1959 | Godfroy | |
| 4,112,936 A | 9/1978 | Blachly | |
| 4,270,531 A | 6/1981 | Blachly et al. | |
| 4,425,911 A | 1/1984 | Luomanen et al. | |
| 4,495,945 A | 1/1985 | Liegner | |
| 5,235,991 A | 8/1993 | Minneman | |
| 5,533,524 A | 7/1996 | Minneman | |
| 5,638,811 A * | 6/1997 | David | 128/207.14 |
| 6,450,167 B1 | 9/2002 | David et al. | |
| 6,890,322 B2 | 5/2005 | Bertoch et al. | |
| D538,926 S | 3/2007 | Jeong et al. | |
| D615,187 S | 5/2010 | Bowden | |
| 2009/0272387 A1 * | 11/2009 | Spencer | 128/848 |
| 2011/0132380 A1 * | 6/2011 | Goldsby | 128/861 |

* cited by examiner

*Primary Examiner* — Patricia Bianco
*Assistant Examiner* — Tarla Patel
(74) *Attorney, Agent, or Firm* — Sutherland Asbill & Brennan LLP

(57) ABSTRACT

A bite block device for use with intrabuccal instruments having a generally U-shaped central body. A lower vestibular rim extends from an outer periphery of a bottom surface of the generally U-shaped central body. A lower lingual rim extends from an inner periphery of the bottom surface of the generally U-shaped central body. An upper vestibular rim extends from an outer periphery of an upper surface of the generally U-shaped central body. An upper lingual rim extends from an inner periphery of the upper surface of the generally U-shaped central body. The upper surface, the upper vestibular rim, and the upper lingual rim are anteriorly discontinuous for a common length to form an intrabuccal instrument channel therethrough.

22 Claims, 2 Drawing Sheets

BITE BLOCK DEVICE

BACKGROUND OF THE INVENTION

1. Field of the Invention

This invention relates to bite blocks. More specifically, it relates to a bite block device for use with intrabuccal instruments.

2. Description of the Related Art

Bite blocks are devices that prop open a patient's oral cavity and prevent the patient from biting down and causing damage within the oral cavity. Bite blocks are divided into two basic groups: (1) those that protect the patient; and (2) those that protect equipment.

An awake patient is not going to bite down and cause trauma because pain will prevent them from doing so. However, a patient that is having a seizure or having a seizure induced, such as with Electro-convulsive therapy (ECT), is not awake and thus can cause damage to tissues. Bite blocks for these situations protect by separating the upper and lower teeth with a rubberized guard that extends from the front incisors to the rear molars.

Bite blocks that protect equipment usually are designed to fit just between the upper and lower incisors and prevent patients from biting down on airway devices. These bite blocks, however, provide minimal or no protection to oral tissues, especially in the molar region.

In traditional cervical spine surgery, patients are anesthetized and pharmacologically paralyzed to allow surgery to be performed. In the last few years, intra-operative nerve monitoring has become the standard of care. During intra-operative neuro monitoring, electrodes are attached to the patient's scalp and then to arms, legs, and other parts of the body. Electrical impulses are sent from the electrodes on the scalp, through the brain, thus stimulating muscle contraction in target areas. This allows technicians to monitor the integrity of the nerves during surgery on the brain and spine. Usually, in this surgery, the patients are anesthetized but not paralyzed. A problem with this stimulation and monitoring is intense Masseter (jaw) muscle contraction, i.e.—the patient bites down intensely, just like a seizure induced by ECT. Because the patient is anesthetized, they cannot protect themselves from injury.

Anesthesia is also maintained with a breathing tube (endotracheal tube) inserted through the patient's mouth into their trachea. This tube is then connected to a ventilator. Biting induced by neuro-stimulation can occlude this breathing tube, endangering the patient.

This scenario dictates the need for a bite block that protects both the patient and the equipment. The current methods of achieving this in most institutions is to make a bite block out of rolled up gauze pads and place them in both sides of the mouth. Unfortunately, this method is less than ideal. Oral trauma is a common complication. Damage can range from minor irritation and pressure damage to severe tongue lacerations requiring further intervention. The gauze pads become misshaped when they get wet from oral secretions. They also become displaced during long and frequent masseter contraction. These inadequacies permit the patient's tongue to migrate between the upper and lower teeth and become severely injured during the procedure.

Accordingly, what is needed is an improved bite block system that protects both the patient and equipment.

SUMMARY OF THE INVENTION

The present invention is directed to a bite block device for use with intrabuccal instruments. The bite block includes a generally U-shaped central body having an anterior portion, a posterior portion, an upper surface for engaging upper teeth of a patient, a lower surface for engaging lower teeth of the patient, and a uniformly graduated height decreasing from the anterior portion to the posterior portion. In use, the generally U-shaped central body is positioned between the upper and lower teeth of the patient.

A lower vestibular rim extends from an outer periphery of the lower surface of the generally U-shaped central body in an arc corresponding to outer surfaces of the lower teeth of the patient. The lower vestibular rim is positioned between the outer surfaces of the lower teeth and the lower cheek or lips of the patient. Similarly, a lower lingual rim extends from an inner periphery of the lower surface of the generally U-shaped central body in an arc corresponding to inner surfaces of the lower teeth of the patient. The lower lingual rim is positioned between the inner surfaces of the lower teeth and the internal portion of the mouth, specifically the tongue.

An upper vestibular rim extends from an outer periphery of the upper surface of the generally U-shaped central body in an arc corresponding to outer surfaces of the upper teeth of the patient. The upper vestibular rim is positioned between the outer surface of the upper teeth and the upper cheek and/or lip of the patient. Similarly, an upper lingual rim extends from an inner periphery of the upper surface of the generally U-shaped central body in an arc corresponding to inner surfaces of the upper teeth of the patient. The upper lingual rim is positioned between the inner surfaces of the upper teeth and the internal portion of the mouth, specifically the tongue.

The upper surface for engaging the upper teeth, the upper vestibular rim, and the upper lingual rim are anteriorly discontinuous for a common length to form an intrabuccal instrument channel therethrough.

These and other features of the claimed bite block will become apparent to one of ordinary skill in the art upon review of the following detailed description when taken in conjunction with the several drawings and claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The present invention is directed to a bite block device for use with intrabuccal instruments. Generally speaking, the bite block is inserted into the mouth of a patient between the upper and lower teeth from the front incisors to the rear molars. The bite block prevents the patient from biting down on their oral tissue, particularly the tongue and cheeks, and allows for the insertion of intrabuccal instruments.

Figure 1:
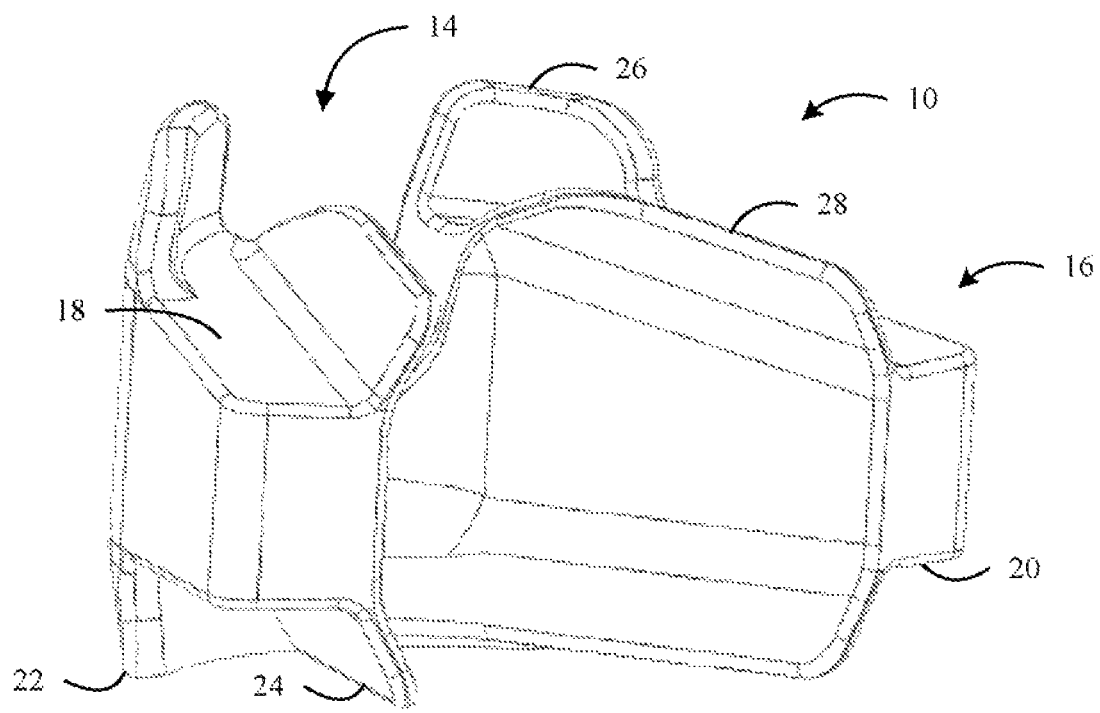
FIG. 1 is a rear upper perspective view of the bite block.
Figure 2:
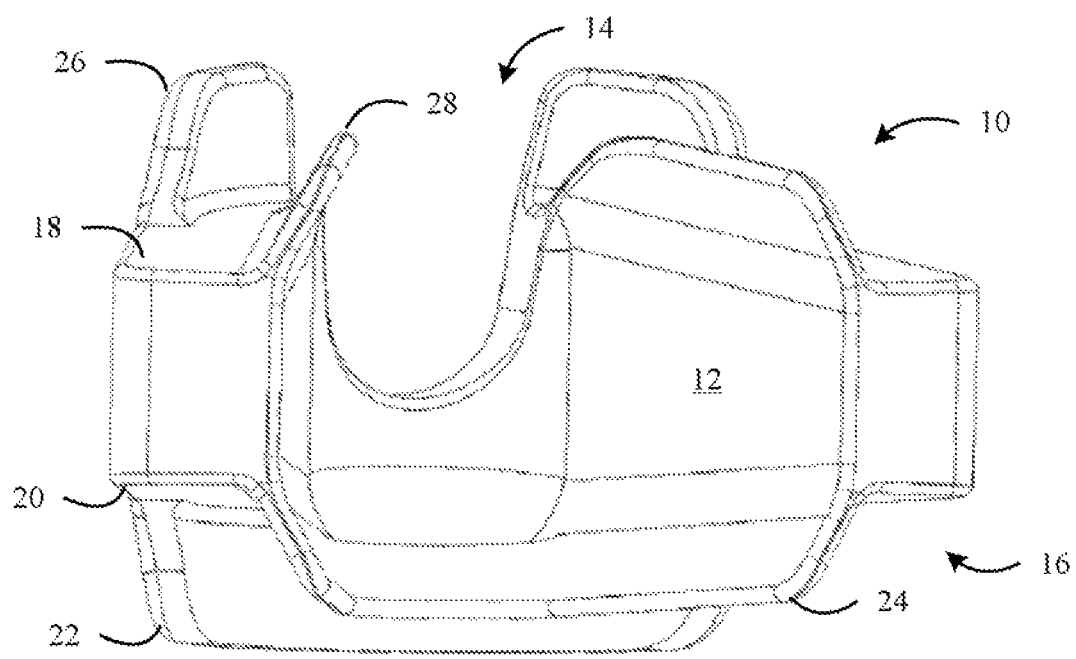
FIG. 2 is a rear side perspective view of the bite block.

Referring to FIGS. 1 and 2, the bite block is generally denoted as reference numeral 10. The bite block 10 includes a generally U-shaped central body 12 having an anterior portion 14, a posterior portion 16, an upper surface 18 for engaging upper teeth of a patient, and a lower surface 20 for engaging lower teeth of the patient. A lower vestibular rim 22 extends from an outer periphery of the lower surface 20 of the generally U-shaped central body 12 in an arc corresponding to outer surfaces of the lower teeth of the patient. A lower lingual rim 24 extends from an inner periphery of the lower surface 20 of the generally U-shaped central body 12 in an arc corresponding to inner surfaces of the lower teeth of the patient. An upper vestibular rim 26 extends from an outer periphery of the upper surface 18 of the generally U-shaped central body 12 in an arc corresponding to outer surfaces of the upper teeth of the patient. An upper lingual rim 28 extends from an inner periphery of the upper surface 18 of the generally U-shaped central body 12 in an arc corresponding to inner surfaces of the upper teeth of the patient.

The generally U-shaped central body is made to conform to the anatomical structure of the patient's teeth and/or gums. In this way, the generally U-shaped curvature of the central body follows the curvature of the teeth and/or gums. The upper and lower surfaces of the generally U-shaped central body may also include planes that correspond to the curve of Spee and curve of Wilson, as are well-known in the art.

The upper and lower vestibular rims are positioned between the outer surfaces of the teeth and the cheek or lips of the patient and mitigate migration of the bite block within the mouth. In an example embodiment, the upper vestibular rim 26 may extend from the upper surface 18 between 5 and 25 mm. In another example embodiment, the lower vestibular rim may extend from the lower surface 20 between 5 and 25 mm. One will appreciate, however, that the range of dimensions of the upper and lower vestibular rims may vary from the above exemplary ranges. Specifically, in certain embodiments, the dimensions of the upper and lower vestibular rims may be tailored to correspond to the anatomy of the patient.

The upper and lower lingual rims are positioned between the inner surfaces of the teeth and the internal portion of the mouth and protect the patient from causing damage within the oral cavity, particularly the tongue. In an example embodiment, the upper lingual rim may extend from the upper surface 18 between 5 and 20 mm. In another example embodiment, the lower lingual rim may extend from the lower surface 20 between 5 and 20 mm. One will appreciate, however, that the range of dimensions of the upper and lower lingual rims may vary from the above exemplary ranges. Specifically, in certain embodiments, the dimensions of the upper and lower lingual rims may be tailored to the anatomy of the patient.

The upper surface, upper vestibular rim, and the upper lingual rim collectively form a channel for the patient's upper teeth. Similarly, the lower surface, lower vestibular rim, and lower lingual rim collectively form a channel for the patient's lower teeth. Depending on the embodiment, both channels may run the entire, or partial, length of the patient's teeth (excluding the intrabuccal instrument channel as discussed below.)

Figure 3:
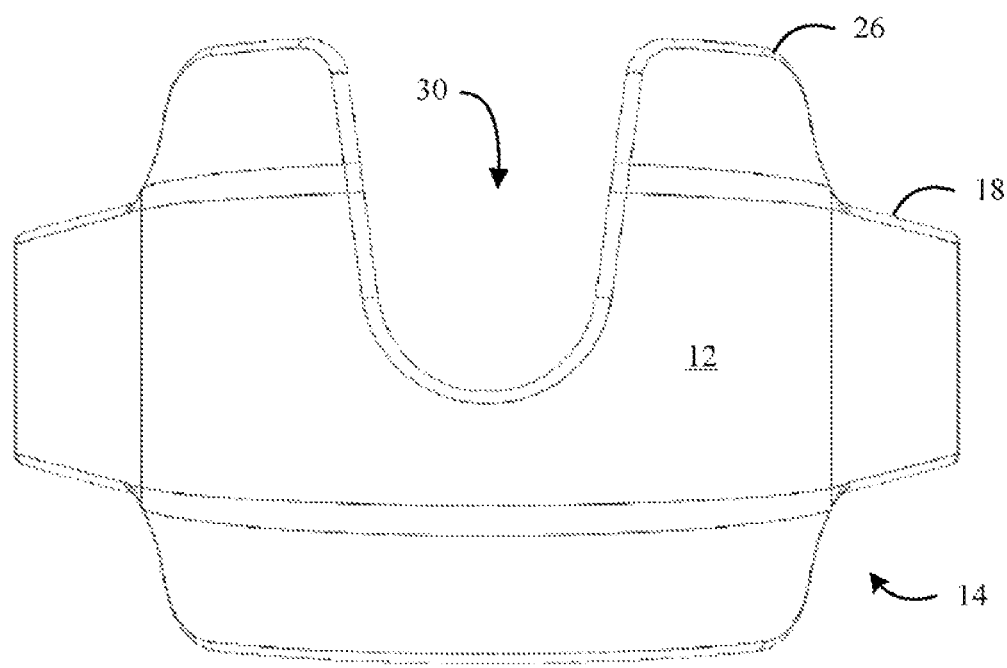
FIG. 3 is a front view of the bite block.

As depicted in FIGS. 2 and 3, the upper surface 18 for engaging the upper teeth, the upper vestibular rim 26, and the upper lingual rim 28 are anteriorly 14 discontinuous for a common length to form an intrabuccal instrument channel 30 therethrough. The intrabuccal instrument channel enables the insertion of intrabuccal instruments, such as a tracheal tube, without removal of the bite block. Although a portion of the upper anterior portion of the bite block is removed, a patient is still unable to bite down in the upper anterior portion due to the remaining upper surface, upper vestibular rim, and upper lingual rim.

The intrabuccal instrument channel may include any shape or size necessary to accommodate a variety of intrabuccal instruments, e.g., in an illustrative embodiment, the intrabuccal instrument channel may be substantially U-shaped (as depicted in FIG. 3) and include a 10 mm width across the discontinuous upper surface and a 10 mm height from the bottom of the U-shape to the plane defined across the discontinuous upper surface. Other exemplary embodiments may include an intrabuccal instrument channel width of between 5 and 20 mm and a height between 5 and 30 mm. Other shapes for the intrabuccal instrument channel may include, but are not limited to, a rectangle, a semi-circle, or a parabola. One will appreciated, however, that the height, width, and shape of the intrabuccal channel may vary from the above exemplary dimensions. Specifically, in certain embodiments, the dimensions of the intrabuccal channel may be tailored to the anatomy of the patient.

Figure 4:
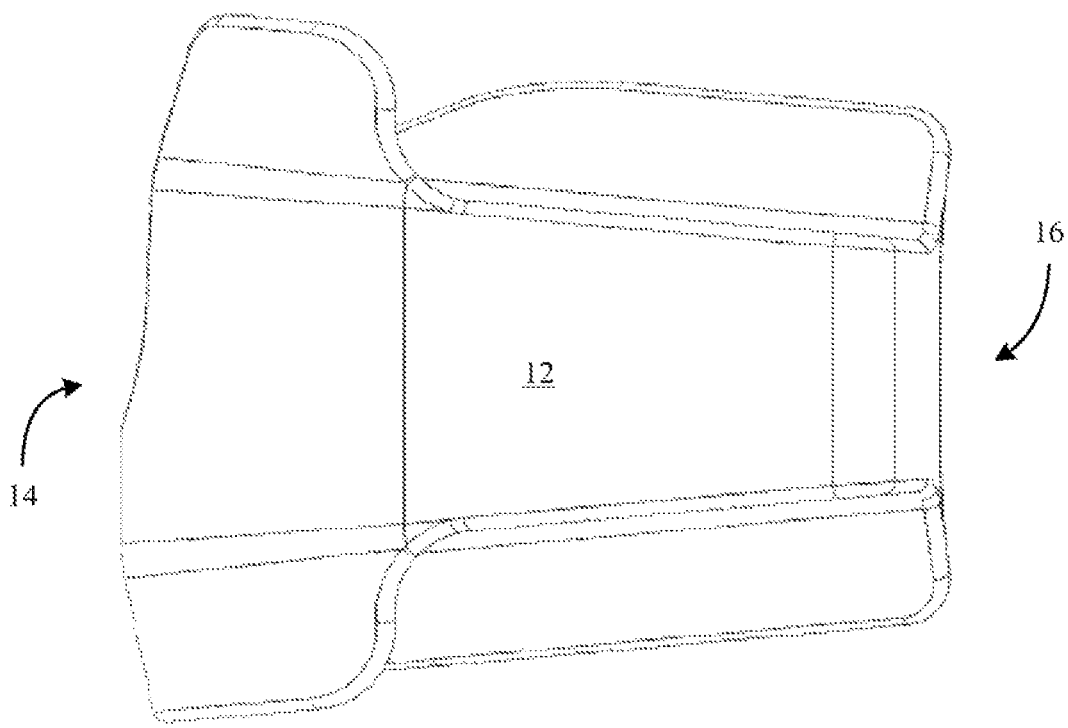
FIG. 4 is a side view of the bite block.

As depicted in FIG. 4, the generally U-shaped central body 12 includes a uniformly graduated height decreasing from the anterior portion 14 to the posterior portion 16. The decreasing height facilitates insertion of the bite block into a patient's mouth and ensures a snug comfortable fit. It also mitigates migration of the bite block within the mouth. For example, in an illustrative embodiment, the posterior portion of the generally U-shaped central body may include a height of at least 5 mm, while the anterior portion of the generally U-shaped central body may include a height of at least 15 mm. Other exemplary embodiments may include the posterior height of the generally U-shaped central body being between about 5 to 25 mm and the anterior height of the generally U-shaped central body being between about 15 to 30 mm. One will appreciated, however, that the range of dimensions of the central body may vary from the above exemplary ranges. Specifically, in certain embodiments, the dimensions of the central body may be tailored to the anatomy of the patient.

Referring back to FIGS. 1 and 2, the upper lingual rim 28 may extend posteriorly beyond the upper vestibular rim 26, and the lower lingual rim 24 may extend posteriorly beyond the lower vestibular rim 22. Moreover, the upper vestibular rim may extend posteriorly between ⅕ to ⅓ the length of the upper surface of the generally U-shaped central body, and the lower vestibular rim may extend posteriorly between ⅕ to ⅓ the length of the lower surface of the generally U-shaped central body.

In an embodiment, the upper lingual rim extends posteriorly at least ½ the length of the upper surface of the generally U-shaped central body. Likewise, the lower lingual rim may extend posteriorly at least ½ the length of the lower surface of the generally U-shaped central body. In another embodiment, the upper lingual rim extends posteriorly the entire length of the upper surface of the generally U-shaped central body. Likewise, the lower lingual rim may extend posteriorly the entire length of the lower surface of the generally U-shaped central body.

As depicted in FIGS. 1, 2, and 4, the upper vestibule rim 26 may be tilted medially inward. For example, the upper vestibule rim may be tilted medially inward between 55 and 85 degrees. Similarly, the upper lingual rim 28 may be tilted medially inward. For example, the upper lingual rim may be tilted medially inward between 45 and 85 degrees.

The lower vestibule rim 22 may be tilted medially inward. For example, the lower vestibule rim 22 may be tilted medially inward between 55 and 85 degrees. Similarly, the lower lingual rim 24 may be tilted medially inward. For example, the lower lingual rim 24 may be tilted medially inward between 45 and 85 degrees.

The tilting of the upper and lower vestibular rims and the upper and lower lingual rims further conforms the bite block to the anatomical structure of the patient's mouth. Moreover, the inward tilting of the upper and lower lingual rims facilities the deflection of the tongue from the teeth. Accordingly, the upper vestibule rim, the lower vestibule rim, the upper lingual rim, and the lower lingual rim may be tilted medially inward anywhere between 0 to 90 degrees.

Those skilled in the art will appreciate that the bite block may be constructed from a variety of different materials. For example, the bite block may be constructed of a suitable metal, a metal alloy, or a suitable resilient material, such as rubber, plastic, or silicon or a combination thereof which are well known in the art of mouth pieces and bite blocks. Preferably, the material will have sufficient strength to resist a patient biting through but be resilient enough that injury to the patient's teeth and/or gums and tongue does not occur. It is also contemplated that the edges of the bite-block be rounded and all surfaces be smoothed to avoid discomfort and possible damage upon insertion and use. Moreover, the bite block may be made of a thermally manipulabe polymer for patient fitting prior to use.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A bite block device for use with intrabuccal instruments, comprising:
   a generally U-shaped central body having an anterior portion, a posterior portion, an upper surface for engaging upper teeth of a patient, and a lower surface for engaging lower teeth of the patient, and a uniformly graduated height decreasing from the anterior portion to the posterior portion;
   a lower vestibular rim extending from an outer periphery of the lower surface of the generally U-shaped central body in an arc corresponding to outer surfaces of the lower teeth of the patient;
   a lower lingual rim extending from an inner periphery of the lower surface of the generally U-shaped central body in an arc corresponding to inner surfaces of the lower teeth of the patient;
   an upper vestibular rim extending from an outer periphery of the upper surface of the generally U-shaped central body in an arc corresponding to outer surfaces of the upper teeth of the patient; and
   an upper lingual rim extending from an inner periphery of the upper surface of the generally U-shaped central body in an arc corresponding to the inner surface of the upper teeth of the patient,
   wherein the upper surface for engaging the upper teeth, the upper vestibular rim, and the upper lingual rim are anteriorly discontinuous for a common length and having a width and a depth below lower surface of the upper teeth to form an intrabuccal instrument channel therethrough,
   wherein the generally U-shaped central body, the lower vestibular rim, the lower lingual rim, the upper vestibular rim, and the upper lingual rim comprise a single unitary piece.

2. The bite block device for use with intrabuccal instruments as in claim 1, wherein the upper lingual rim extends posteriorly beyond the upper vestibular rim.

3. The bite block device for use with intrabuccal instruments as in claim 1, wherein the upper vestibular rim extends posteriorly between ⅕ to ⅓ the length of the upper surface of the generally U-shaped central body.

4. The bite block device for use with intrabuccal instruments as in claim 1, wherein the lower lingual rim extends posteriorly beyond the lower vestibular rim.

5. The bite block device for use with intrabuccal instruments as in claim 1, wherein the lower vestibular rim extends posteriorly between ⅕ to ⅓ the length of the lower surface of the generally U-shaped central body.

6. The bite block device for use with intrabuccal instruments as in claim 1, wherein the upper lingual rim extends posteriorly at least ½ the length of the upper surface of the generally U-shaped central body.

7. The bite block device for use with intrabuccal instruments as in claim 1, wherein the upper lingual rim extends posteriorly the entire length of the upper surface of the generally U-shaped central body.

8. The bite block device for use with intrabuccal instruments as in claim 1, wherein the lower lingual rim extends posteriorly at least ½ the length of the lower surface of the generally U-shaped central body.

9. The bite block device for use with intrabuccal instruments as in claim 1, wherein the lower lingual rim extends posteriorly the entire length of the lower surface of the generally U-shaped central body.

10. The bite block device for use with intrabuccal instruments as in claim 1, wherein the intrabuccal instrument channel includes a width between 5 and 20 mm.

11. The bite block device for use with intrabuccal instruments as in claim 1, wherein the posterior portion of the generally U-shaped central body has a height between 5 and 25 mm.

12. The bite block device for use with intrabuccal instruments as in claim 1, wherein the anterior portion of the generally U-shaped central body has a height between 15 and 30 mm.

13. The bite block device for use with intrabuccal instruments as in claim 1, wherein the posterior portion of the generally U-shaped central body has a height between about 5 and 25 mm and the anterior portion of the generally U-shaped central body has a height between about 15 and 30 mm.

14. The bite block device for use with intrabuccal instruments as in claim 1, wherein the upper vestibule rim extends between 5 and 25 mm medially inward in relation to the upper surface of the generally U-shaped central body.

15. The bite block device for use with intrabuccal instruments as in claim 14, wherein the upper vestibule rim is tilted medially inward between 0 and 90 degrees.

16. The bite block device for use with intrabuccal instruments as in claim 1, wherein the upper lingual rim extends between 5 and 20 mm medially inward in relation to the upper surface of the generally U-shaped central body.

17. The bite block device for use with intrabuccal instruments as in claim 16, wherein the upper lingual rim is tilted medially inward between 0 and 90 degrees.

18. The bite block device for use with intrabuccal instruments as in claim 1, wherein the lower vestibule rim extends between 5 and 25 mm medially inward in relation to the lower surface of the generally U-shaped central body.

19. The bite block device for use with intrabuccal instruments as in claim 18, wherein the lower vestibule rim is tilted medially inward between 0 and 90 degrees.

20. The bite block device for use with intrabuccal instruments as in claim 1, wherein the lower lingual rim extends between 5 and 20 mm medially inward in relation to the lower surface of the generally U-shaped central body.

21. The bite block device for use with intrabuccal instruments as in claim 20, wherein the lower lingual rim is tilted medially inward between 0 and 90 degrees.

22. The bite block device for use with intrabuccal instruments as in claim 1, wherein the intrabuccal instrument channel is generally U-shaped.

\* \* \* \* \*